United States Patent
Shah

(12) 
(10) Patent No.: US 6,291,543 B1
(45) Date of Patent: Sep. 18, 2001

(54) SURFACIALLY CROSS-LINKED ELASTOPLASTIC ARTICLES, AND METHOD OF MAKING THE SAME

(75) Inventor: Tilak M. Shah, Cary, NC (US)

(73) Assignee: Polyzen, Inc., Cary, NC (US)

( * ) Notice: Subject to any disclaimer, the term of this patent is extended or adjusted under 35 U.S.C. 154(b) by 0 days.

(21) Appl. No.: 09/578,050

(22) Filed: May 24, 2000

(51) Int. Cl.$^7$ .................................................. C08F 2/46
(52) U.S. Cl. ................ 522/162; 522/174; 522/176; 522/181; 522/134; 522/135; 522/136; 522/138; 522/140; 522/142; 522/144; 522/6; 522/33; 522/39; 522/36; 522/40; 522/43; 522/44; 522/47; 522/46
(58) Field of Search ..................... 522/6, 33, 36, 522/39, 40, 43, 44, 46, 47, 102, 104, 114, 116, 119, 120, 121, 122, 126, 149, 162, 174, 176, 181, 134, 135, 136, 138, 140, 142, 143, 144

(56) References Cited

U.S. PATENT DOCUMENTS

| | | |
|---|---|---|
| 4,414,372 | 11/1983 | Farnham et al. . |
| 4,444,816 * | 4/1984 | Richards et al. ..................... 428/36 |
| 4,626,458 * | 12/1986 | Pithouse et al. ..................... 428/36 |
| 4,711,942 | 12/1987 | Webster . |
| 4,771,116 | 9/1988 | Citron . |
| 5,019,634 | 5/1991 | Boettcher et al. . |
| 5,021,524 | 6/1991 | Dicker et al. . |
| 5,274,028 * | 12/1993 | Bertrand et al. ..................... 525/17 |
| 5,786,426 * | 7/1998 | Sperling et al. ..................... 525/131 |
| 5,965,630 | 10/1999 | Imafuko et al. . |
| 5,965,631 | 10/1999 | Nicolson et al. . |
| 5,993,415 * | 11/1999 | O'Neil et al. ........................ 604/96 |

FOREIGN PATENT DOCUMENTS

| | | |
|---|---|---|
| 262 629 B1 | 4/1988 | (EP) . |
| 0 849 296 A2 | 6/1998 | (EP) . |

OTHER PUBLICATIONS

Encyclopedia of Polymer Science and Engineering, John Wiley & Sons, vol. 7, p. 580, 1987.

Journal American Chemical Society, Urszula Kolczek, Gunther Rist, Jurt Dietliker and Jakob Wirz, "Reaction Mechanism of Monoacyl–and Bisacylphosphine Oxide Photo initiators Studied by P–, C–, and H–DICNP and ESR", 1996, 118, 6477–6489.

* cited by examiner

Primary Examiner—James J. Seidleck
Assistant Examiner—Sanza L. McClendon
(74) Attorney, Agent, or Firm—Steven J. Hultquist

(57) ABSTRACT

A surfacially ultraviolet radiation-crosslinked article formed of a homogeneous composition including an elastoplastic material, a cross-linker component that is cross-linkable by free-radical polymerization, and a free-radical source material generating free radicals in exposure to ultraviolet radiation, wherein the elastoplastic material is surfacially cross-linked by exposure to ultraviolet radiation, wherein the sub-surface bulk volume of the article is non-cross-linked, and the article is resiliently deformable from and resiliently recoverable to a shape of the article when it was exposed to ultraviolet radiation for surfacial cross-linking thereof. The article is particularly amenable to embodiment as a catheter, or other similar medical device for cardiovascular or other medical procedures.

36 Claims, 2 Drawing Sheets

SURFACIALLY CROSS-LINKED ELASTOPLASTIC ARTICLES, AND METHOD OF MAKING THE SAME

BACKGROUND OF THE INVENTION

1. Field of the Invention

The present invention relates to surfacially cross-linked articles, of a type useful in catheter applications, and to a novel method of making such surfacially cross-linked articles.

2. Description of the Related Art

Catheters are widely utilized in a variety of medical interventions in which material is transported to a corporeal locus, e.g. within the vascular system.

The catheter in such applications must be translated through a corporeal lumen, and therefore must be of a flexible character. At the same time, the catheter must possess sufficient structural rigidity to prevent collapse or even partial occlusion as a result of being "threaded" through the tortuous path of the vasculature.

Catheters may be of widely varying type. Catheters are used for example in angioplasty, including guide catheters for procedures such as balloon or laser angioplasty. In some applications, the use of the catheter requires a particular shape or shaping capability.

An example is the Judkins catheter whose distal portion is inserted into the left coronary artery during cardiac intervention. The Judkins catheter is shaped (by heat-forming) with a main straight portion and a curved distal portion, so that its overall form is of generally "J"-shape. The curvate character of the distal portion of the Judkins catheter requires that it have sufficient flexibility to be distended to a linear conformation, and that when introduced into the left coronary arterial locus the distal portion returns to its curvate form (for entry into the ostium of the coronary artery). Catheters of the foregoing types thus require a concurrent flexibility/rigidity enabling the distension of the catheter, with subsequent recovery of an initial shape when the distending force is discontinued.

The art continues to seek improvement in catheter articles.

SUMMARY OF THE INVENTION

The present invention relates to a surfacially cross-linked article and to a method of making the same. The article can be embodied as a catheter or other article that in use requires concurrent flexibility and shape recovery upon deformation and subsequent release of the deforming force.

The surfacial cross-linking in accordance with the invention also is usefully employed to increase hardness or stiffness of the product article, and such hardness or stiffness properties can be selectively imparted to different portions of the product article, by cross-linking the respective surfaces of such portions of the product article to differing extents.

In one aspect, the invention relates to surfacially ultraviolet radiation-cross-linked article formed of a homogeneous composition including an elastoplastic material, a cross-linker component that is cross-linkable by free-radical polymerization, and a free-radical source material generating free radicals in exposure to ultraviolet radiation, wherein the homogeneous composition is surfacially cross-linked by exposure to ultraviolet radiation, wherein the sub-surface bulk volume of the article is non-cross-linked, and wherein the article is resiliently deformable from and resiliently recoverable to an initial shape of the article, e.g., the shape of the article when it was exposed to ultraviolet radiation for surfacial cross-linking thereof.

In another aspect, the invention relates to a method of fabricating a surfacially ultraviolet radiation-cross-linked article, comprising the steps of: forming a precursor structure for the article of a homogeneous composition including an elastoplastic material, a cross-linker component that is cross-linkable by free-radical polymerization, and a free-radical source material generating free radicals in exposure to ultraviolet radiation, and exposing a surface of the precursor structure to ultraviolet radiation for sufficient time and under sufficient radiation intensity to surfacially cross-link the composition, to yield the surfacially ultraviolet radiation-cross-linked article, wherein the sub-surface bulk volume of the article is non-cross-linked, and the article is resiliently deformable from and resiliently recoverable to a shape of the precursor structure, e.g., the shape it possessed when it was exposed to ultraviolet radiation for Surfacial cross-linking thereof.

Other aspects, features and embodiments of the invention will be more fully apparent from the ensuing disclosure and appended claims.

Figure 1:
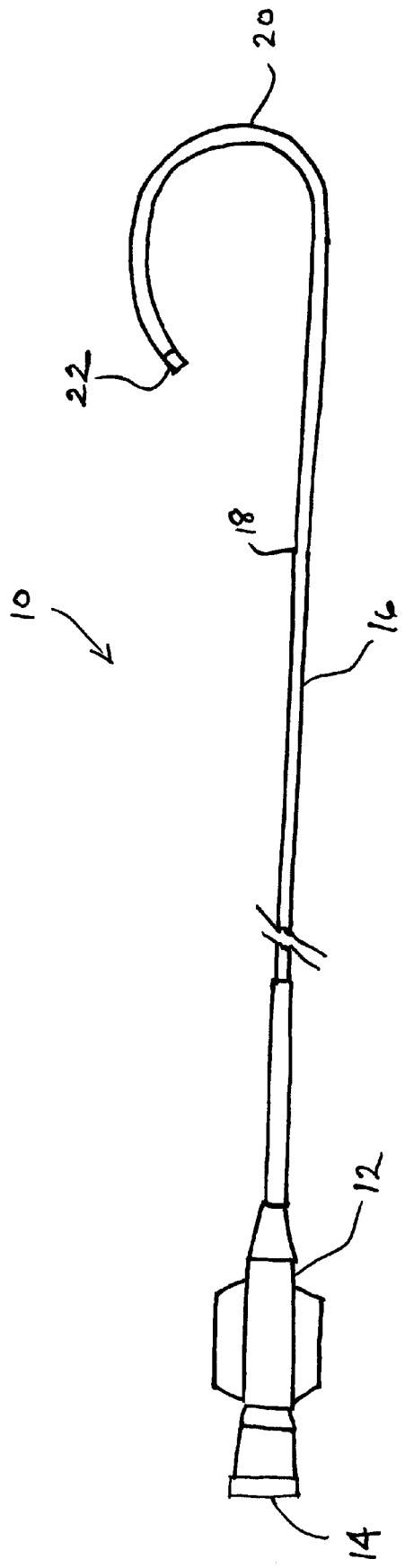
FIG. 1 is a schematic representation of a catheter according to one embodiment of the invention.

DETAILED DESCRIPTION OF THE INVENTION,

AND PREFERRED EMBODIMENTS THEREOF

The article of the present invention is amenable to embodiment in a wide variety of confirmations and structural forms. For example, the article of the invention may be of block, cylindrical, ribbon, fiber or tubular forms, or may be embodied in any other form suitable for the intended end use of the article.

In one application, the article is embodied for medical catheter use and is of tubular form. The catheter can be fabricated as a Judkins catheter, having a generally J-shaped tubular form, e.g., comprising a main linear portion and a distal curvate portion.

As used herein, the term "surfacially" in reference to the ultraviolet radiation-cross-linked particle of the invention refers to the article being, UV-cross-linked on a surface region thereof. Such surface region may be only a portion of the overall surface area of the article, or alternatively the entire surface may be UV-cross-linked in character. The UV-crosslinking of the invention is surfacial in character, in that the irradiated surface is cross-linked, but the underlying bulk volume of the article is non-cross-linked.

As used herein, the term "elastoplastic" used in reference to the material of which the article of the invention is formed, means a material which is polymeric and elastic in character, recovering at least a major portion of its original shape (and dimensional character) after being subjected to a deforming force and then released from such force. The elastoplastic material therefore is resiliently deformable from and resiliently recoverable to an original shape of the article (i.e., the shape it had at the time it was exposed to the ultraviolet radiation for surfacial cross-linking thereof).

It will be appreciated that the surfacial cross-linking of the article of the invention may be carried out at varied UV radiation exposure times and UV radiation intensity, as necessary or desirable to achieve a surfacially ultraviolet radiation-cross-linked article for a specific end use.

The invention is based on the discovery that an article formed of cross-linkable flexible resilient material can be cross-linked only at its surface region, with the bulk material underlying the cross-linked surface layer being non-cross-linked, to achieve an enhanced rigidification of the structural article, while retaining the bulk flexible resilient properties of the structure.

Such surface cross-linking in application to a tubular catheter article of appropriate composition enables the fabrication of a catheter that is readily deformable in translation through the vascular pathway, but retains sufficient strength to avoid collapse or occlusion of the central lumen of the catheter. The catheter of such fabrication has a "memory" character, so that the original shape (prior to insertion into the corporeal lumen) is readily recovered at the corporeal locus of use.

This memory character is highly advantageous for a catheter such as a Judkins catheter, requiring insertion into the left coronary artery, or otherwise for a product article that in pre-use deployment must be deformed or distended from an original conformation, and must recover that original conformation at the locus of use.

The surfacially ultraviolet radiation-cross-linked article of the invention is formed of a homogeneous composition, and thereby differentiates from multi-layer or composite structures that require greater investments of time, effort and expense in their manufacture.

By use of a homogeneous composition the article of the invention can readily be formed as a unitary body of appropriate shape, for subsequent UV radiation exposure and surfacial cross-linking.

The homogeneous composition for the article of the invention includes an elastoplastic material, a cross-linker component that is cross-linkable by free-radical polymerization, and a free-radical source material generating free radicals in exposure to ultraviolet radiation.

The elastoplastic material may be of any suitable type, and can be a polymer such as a polyester, polyamide, polyurethane, polyether/polyamide block copolymer, plasticized polyvinylchloride, etc., as well as being a blended material such as a compatible blend of two or more polymeric materials.

The cross-linker component utilized in the homogeneous composition of the invention likewise may be of any suitable type. Illustrative examples of cross-linkers that can be usefully employed in various embodiments of the invention include compounds containing functional groups such as acryl, (meth) acryl, vinyl, propenyl, butenyl, pentenyl, hexenyl, octenyl, allyl, alkenyloxy, alkenylamino, allyloxy, allylamino, furanyl, phenyl and benzyl groups. The cross-linker desirably contains an ethylenically unsaturated moiety such as vinyl or allyl. Examples of specific cross-linker compounds include trimethylolpropane triacrylate, triallyl cyanurate, melamine cross-linkers (usefully employed with urethane polymers), tolylene 2,4-diisocyanate cross-linkers (for acrylic copolymers), organohydrogenpolysiloxane cross-linkers (for silicone polymers), epoxy cross-linkers, etc.

The free-radical source material in the homogeneous composition comprises a material generating free-radicals in exposure to ultraviolet radiation. Such free-radical source materials include photoinitiators, such as benzoin, substituted benzoins such as benzoin ethyl ether, benzophenone, benzopheone derivatives, Michler's ketone, alplhahydroxyketone, benzildimethylketal, isopropylthioxanthane, dialkoxyacetophelnones such as diethoxyacetophenone, acetophenone, benzil, and other derivatives (substituted forms) and mixtures thereof.

The relative amounts of the cross-linker component and free-radical source material relative to the elastoplastic material, may be widely varied in the practice of the invention. Particularly suitable compositions may be readily empirically determined by simple formulation and UV irradiation tests to determine the ultimate physical and chemical properties of the final surfacially cross-linked material and product article comprising same. In general, the photoinitiator concentration will be in a range of about 0.1% to about 65% by weight, and more specifically and preferably from about 0.2% to about 50% by weight, based on the weight of the cross-linker component.

The photointiator employed in the homogeneous composition may be polymer-bound, and may in fact be bound to the elastoplastic material.

The cross-linker component is present in the homogeneous composition at any suitable concentration. In preferred practice of the invention, the cross-linker has a concentration of from about 1% to about 20% by weight, based on the weight of the elastoplastic material present in the composition.

The homogeneous composition may also include other ingredients to modify the ultimate properties of the article, as necessary or desirable for a specific end use application.

Fillers or reinforcing materials may be usefully employed in compositions of the present invention to provide enhanced mechanical properties or other specific functional properties, and in some instances to enhance UV radiation surface curability of the composition.

Preferred fillers include radioopaque fillers such as barium sulfate, bismuth trioxide, bismuth oxychloride, bismuth subcarbonate, tungsten powder, and combinations and compatible blends thereof. Radioopaque fillers have the advantage that they enable the catheter to be readily visualized in the body by fluoroscopic techniques and on x-ray film for therapeutic monitoring and diagnostic radiology.

As a fortuitous concurrent advantage in the practice of the present invention, the use of a radioopaque filler permits a high degree of control of the depth of cross-linking of the surface of the article, so that only a very shallow surface layer is cross-linked (i.e., the radioopaque filler prevents a significant depth of penetration of incident UV radiation in the bulk interior volume of the composition).

Alternatively, the homogeneous composition may include other UV radiation blocking or scattering components, whose concentration will determine the extent of cross-linking in the material of the article subjected to UV radiation.

Among non-radioopaque fillers, a wide variety of other materials may be used for filling or reinforcement of the composition. Preferred fillers include reinforcing silicas, such as fumed silicas, which may be untreated (hydrophilic) or treated to render them hydrophobic in character.

In general, fillers may be employed at any suitable concentration in the cross-linkable composition, but generally are present at concentrations of from about 5 to about 45% by weight, based on the weight of the elastoplasic material. Generally, any other suitable mineralic, carbonaceous, glass or ceramic fillers may be potentially advantageously employed. Examples include ground quartz, tabular alumina, diatomaceous earth, silica balloons, calcium carbonate, carbon black, titanium oxide, aluminum oxide, aluminum hydroxide, zinc oxide, glass fibers, etc.

The homogeneous composition may further include any suitable additives, such as UV stabilizers (e.g., UV stabilizers commercially available from Ciba-Geigy, Inc. under the trademarks Chimassorb and Tinuvin), antioxidants (e.g., those commercially available from Ciba-Geigy, Inc. under the trademark Irganox), colorants, pigments, etc.

The homogeneous composition of the invention may be prepared in any suitable manner, involving blending or combining the respective elastoplastic material, cross-linker and free-radical source ingredients to form a homogeneous composition that subsequently may be processed into a precursor structure, the term "precursor structure" meaning the structure that is exposed to ultraviolet radiation to surface cross-link the surface thereof to form the product radiation-cross-linked article.

The homogeneous composition thus may be formulated by any suitable mixing or blending technique, e.g., agitation by mechanical stirring, sonification treatment, translation through a static mixer device, or in any other suitable manner to achieve a state of homogeneity for the composition. The composition can be further melt-blended using a single or twin screw extruder, then pelletized, dried and processed into a specific product.

More generally, the homogeneous composition can be processed in any suitable conventional manner appropriate to the end use article, e.g., by injection molding, casting, extrusion (e.g., of tubing, profile or film), rotational molding, blow molding, etc.

In preferred practice for manufacture of catheter articles, the homogeneous composition after its formulation is compounded and pelletized, then formed by extrusion into tubing or other precursor structure.

Once the precursor structure is formed, the desired surface area of the precursor structure is exposed to UV radiation of suitable intensity for an appropriate period of time. For catheter precursor structures, the surfacial cross-linking can be effected by UV light exposure for a period of 30 seconds to 10 minutes at a radiation intensity of from about 300 microwatts per square centimeter to about 30,000 microwatts per square centimeter. It will be appreciated that there is an inverse correlation of exposure time and UV light intensity, with higher UV intensity generally requiring shorter exposure periods, and vice versa. In some instances, depending on the UV intensity of the radiation to which the precursor structure is exposed, it can be advantageous to employ more restricted radiation intensity values, e.g., in the range of from about 600 to about 26, 000 microwatts per square centimeter, or even a narrower range of from about 4,000 to about 20,000 microwatts per square centimeter.

By surfacial cross-linking, the precursor structure is converted to the product article. As a result, the shape of the article is appropriately "set" by the surfacial cross-linking, and the article thereafter will retain "memory" and elastically recover its initial shape when a deforming force is removed from the article subsequent to distension of the article under the applied deforming force.

The UV radiation cross-linking employed in accordance with the present invention is markedly superior to the use of heat for shaping the precursor article, since the heat required may be detrimental to the properties desired in the product article, as well as requiring substantially more time, effort and expense in relation to the surfacial cross-linking approach of the present invention.

In consequence of the memory capability of the product article, a shaped article can be readily formed and subsequently usefully employed. For example, a Judkins catheter can be formed in accordance with the invention by constraining the catheter in a curved conformation at its distal end, and exposing it to appropriate UV radiation exposure. Thereafter, such catheter can be straightened at its distal end portion from its initial generally "J"-shaped conformation, to accommodate insertion and threading through the vascular network to the left coronary artery, at which locus the removal of the distending confinement of the vasculature will allow the catheter to reconform to the "J", shape.

The ultraviolet radiation cross-linking utilized in fabricating the article of the present invention is superior to cross-linking mediated by other forms of radiation, such as e-beam or gamma radiation. Specifically, e-beam or gamma radiation cross-linking is difficult to control with respect to cross-linking only a surfacial region of the precursor structure. Additionally, it is difficult and expensive to deploy small-sized e-beam or gamma radiation units, and both forms of radiation have significant associated safety hazards. Further, in application to catheter manufacture, e-beam or gamma radiation poses implementationial difficulties since it needs to be implemented in a production mode as an intermediate step following the curving of the catheter, in the manufacture of Judkins catheters or other catheters having curvate structure.

Referring now to the drawings, FIG. 1 is a schematic view of a catheter article 10 according to one embodiment of the present invention.

The catheter article 10 as shown includes a hub 12 that is connectable at its proximal end 14 to an angiographic syringe (not shown) or other source of material or components to be transmitted through the catheter to the target corporeal locus.

The catheter article 10 comprises a tubular member 16 including a main straight section 18 and a distal "J"-shaped portion 20 terminating in a tip element 22.

Figure 2:
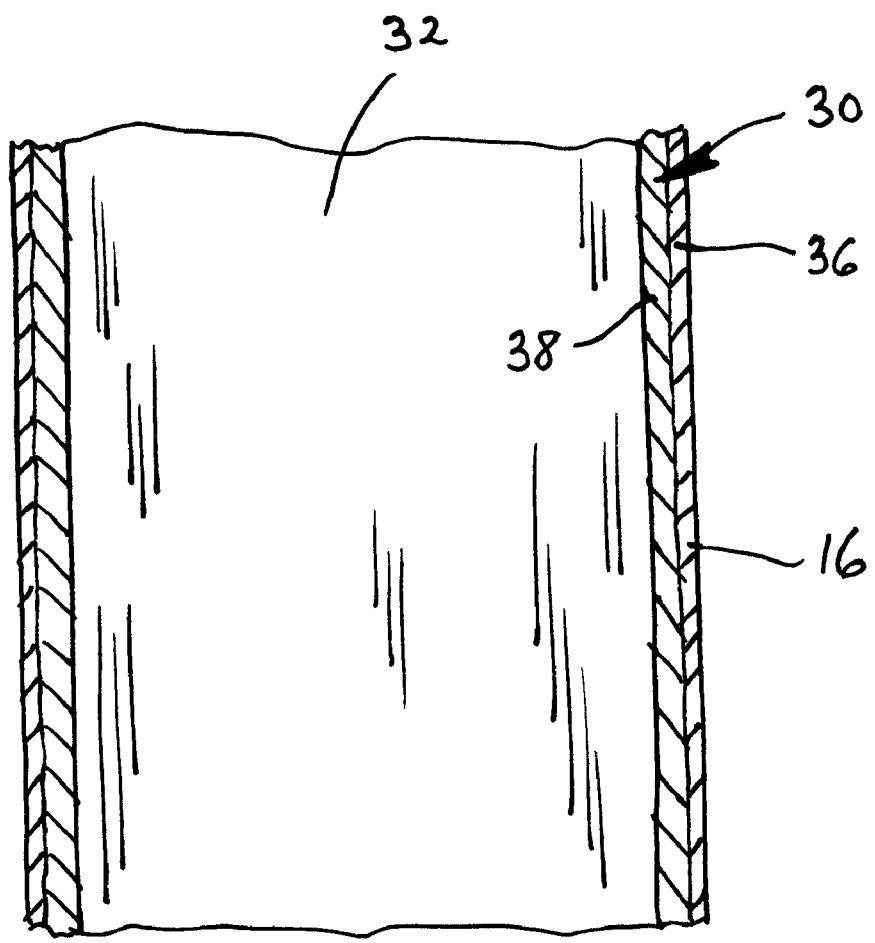
FIG. 2 is a sectional elevational view of the catheter of FIG. 1.

FIG. 2 is a cross-sectional elevation view of a portion of the tubular member 16 of the catheter article 10 of FIG. 1 as shown, the tubular member 16 comprises a wall member 30 bounding a central lumen 32 of the catheter article, to accommodate passage of the material to be transported to the patient, through the lumen of the catheter article.

The wall of the catheter article has a cross-linked surface layer 36 and a non-cross-linked sub-surface layer 38. The depth of the cross-linked layer 36 is sufficiently deep to impart a "set" or fixated character to the tubular element 16.

Referring again to FIG. 1, it will be appreciated that the straight portion 18 and curvate portion 20 of the catheter article may be differentially irradiated in respect of one another-, to yield different surfacial cross-linking in the respective portions. For example, the straight portion may be irradiated for differing time/intensity conditions than the curvate portion, so that a different extent of cross-linking and a different rigidity are imparted, e.g., with the curvate portion having a higher or lower density of cross-linking than the straight portion.

The rigidity or "set" of the surfacially cross-linked product article nonetheless is adequate to permit ready flexural and translational movement of the article, with resilient recovery of the original shape when the flexural or translational force is removed.

In this manners the flexing of the curvate portion 20 of the catheter article 10 in FIG. 1 to straighten same will permit threading into the arterial lumen, but upon release of the straightening pressure, the curvate portion will recover the shape illustrated in FIG. 1

The features and advantages of the invention are more fully shown by the following illustrative examples, which are not to be construed in any limiting sense, as regards the broad scope of the present invention.

EXAMPLE

Catheter articles of conventional length and diameter characteristics were formed from each of the Sample 1–Sample 5 formulations identified in Table 1 below.

TABLE 1

| SAMPLE | 1 | 2 | 3 | 4 | 5 |
|---|---|---|---|---|---|
| Resin | 70 | 100 | 100 | 100 | 100 |
| Bis Subcarbonate Filler | 30 | 0 | 0 | 0 | 0 |
| UV Cross-Linker | 5 | 5 | 5 | 5 | 5 |
| UV Initiator | 3 | 1 | 1 | 1 | 1 |
| Pigment-TiO$_2$ | 0.2 | 0 | 0 | 0 | 0 |
| Pigment-Phthaloblue | 0.2 | 0 | 0 | 0 | 0 |
| UV Stabilizer | 0.5 | 0.5 | 0.5 | 0.5 | 0.5 |

The resin used in Samples 1 and 2 was Arnitel 67D polyester resin, commercially available from DSM Corporation.

Sample 3 included Pebax® 70D Polyether/Polyamide block copolymer, commercially available from Atochem, Inc.

Sample 4 included Pellethane 2363 75D polyurethane resin, commercially available from Dow Chemical Company.

The resin used in Sample 5 was Rilsan AESNO TL polyamide resin commercially available from Atochem, Inc.

The UV cross-linker in all samples was trimethylolpropane triacrylate.

The UV initiator in all samples was benzophenone.

The UV stabilizer in all samples was Tinuvin P commercially available from Ciba-Geigy, Inc.

Each of the Table 1 compositions for the respective Samples 1–5 was extruded to form tubing, which then was bent into a curvate shape and exposed to UV radiation, using an Ultracure 100 SS ultraviolet lamp having an intensity of 24,000 microwatts (commercially available from EFOS, Inc.).

The shaped tube of Sample 1 was exposed to radiation for 5 minutes, the shaped tube of Sample 2 for 3 minutes, the shaped tube of Sample 3 for 2 minutes, the shaped tube of Sample 4 for 2 minutes, and the shaped tube of Sample 5 for 2 minutes.

In all cases, surfacial cross-linking was effected. Subsequently, after distension of the curvate tube to a linear conformation, release of the distending pressure resulted in full recovery of the curvate shape at which the tube was originally set by UV radiation exposure, in all cases.

Although the invention has been variously disclosed herein with reference to illustrative aspects, embodiments and features, it will be appreciated that the aspects, embodiments and features described hereinabove are not intended to limit the invention, and that other variations, modifications and other embodiments will suggest themselves to those of ordinary skill in the art. The invention therefore is to be broadly construed, consistent with the claims hereafter set forth.

What is claimed is:

1. A surfacially ultraviolet radiation-cross-linked article formed of a homogeneous composition including an elastoplastic material, a cross-linker component that is cross-linkable by free-radical polymerization, and a free-radical source material generating free radicals in exposure to ultraviolet radiation, wherein the homogeneous composition is surfacially cross-linked by exposure to ultraviolet radiation, wherein the sub-surface bulk volume of the article is non-cross-linked, and the article is resiliently deformable from and resiliently recoverable to an initial shape of the article.

2. The article of claim 1, wherein the elastoplastic material comprises a polymer selected from the group consisting of polyesters, polyamides, polyurethanes, polyether/polyamide block copolymers, plasticized polyvinylchlorides, and compatible blends of two or more of the foregoing.

3. The article of claim 1, wherein the elastoplastic material comprises a polyester.

4. The article of claim 1, wherein the elastoplastic material comprises a polyurethane.

5. The article of claim 1, wherein the elastoplastic material comprises a polyether/polyamide block copolymer.

6. The article of claim 1, wherein the elastoplastic material comprises a polyamide.

7. The article of claim 1, wherein the homogeneous composition comprises a radioopaque filler.

8. The article of claim 7, wherein the radioopaque filler comprises a filler selected from the group consisting of barium sulfate, bismuth trioxide, bismuth oxychloride, bismuth subcarbonate, tungsten powder, and combinations of two or more of the foregoing.

9. The article of claim 1, wherein the homogeneous composition filler comprises one or more components selected from the group consisting of uv stabilizers, antioxidants, colorants, pigments, non-radioopaque fillers, and compatible combinations of two or more of the foregoing.

10. The article of claim 1, wherein the cross-linker component comprises one or more of compounds containing functional groups selected from the group consisting of acryl, (meth) acryl, vinyl, propenyl, butenyl, pentenyl, hexenyl, octenyl, allyl, alkenyloxy, alkenylamino, allyloxy, allylamino, furanyl, phenyl and benzyl.

11. The article of claim 1, wherein the cross-linker component is selected from the group consisting of triallyl cyanurate, trimethylolpropane triacrylate, melamine cross-linkers, tolylene 2,4-diisocyanate, organohydrogenpolysiloxane cross-linkers, and epoxy cross-linkers.

12. The article of claim 1, wherein the free radical source material comprises one or more of benzoin, substituted benzoins, benzopheone, benzopheone derivatives, Michler's ketone, alphahydroxyketone, benzildimethylketal, isopropylthioxanthane, dialkoxyacetophenones, acetophenone, benzil, and other derivatives (substituted forms) and mixtures thereof.

13. The article of claim 1, comprising a tubular article whose outer tubular surface is surfacially cross-linked.

14. The article of claim 1, comprising a generally J-shaped tubular article.

15. The article of claim 1, of tubular form.

16. The article of claim 14, comprising a main linear portion and a distal curvate portion, wherein the distal curvate portion is differently surfacially cross-linked than the main linear portion.

17. The article of claim 1, wherein said article been constrained in a curved conformation as said initial shape of the article, and exposed in the constrained curved conformation to said ultraviolet radiation.

18. The article of claim 1, wherein the elastoplastic material comprises polyester, polyamide, polyurethane or a polyether/polyamide block copolymer, the cross-linker component comprises trimethylol propane triacrylate or triallylcyanurate, and the free-radical source material comprises benzophenone or benzildimethylketal.

19. A method of fabricating a surfacially ultraviolet radiation-crosslinked article, comprising the steps of: forming a precursor structure for the article of a homogeneous composition including an elastoplastic material, a cross-linker component that is cross-linkable by free-radical polymerization, and a free-radical source material generating free radicals in exposure to ultraviolet radiation, and exposing a surface of the precursor structure to ultraviolet radiation for sufficient time and under sufficient radiation intensity to surfacially cross-link the composition, to yield the surfacially ultraviolet radiation-crosslinked article, wherein the sub-surface bulk volume of the article is non-cross-linked, and the article is resiliently deformable from and resiliently recoverable to a shape of the precursor structure when it was exposed to ultraviolet radiation for surfacial cross-linking thereof.

20. The method of claim 19, wherein the elastoplastic material comprises a polymer selected from the group consisting of polyesters, polyamides, polyurethanes, polyether/polyamide block copolymers, plasticized polyvinylchlorides, and compatible blends of two or more of the foregoing.

21. The method of claim 19, wherein the elastoplastic material comprises a polyester.

22. The method of claim 19, wherein the elastoplastic material comprises a polyurethane.

23. The method of claim 19, wherein the elastoplastic material comprises a polyether/polyamide block copolymer.

24. The method of claim 19, wherein the elastoplastic material comprises a polyamide.

25. The method of claim 19, wherein the homogeneous composition comprises a radioopaque filler.

26. The method of claim 25, wherein the radioopaque filler comprises a filler selected from the group consisting of barium sulfate, bismuth trioxide, bismuth oxychloride, bismuth subcarbonate, tungsten powder, and combinations of two or more of the foregoing.

27. The method of claim 19, wherein the homogeneous composition further comprises one or more components selected from the group consisting of uv stabilizers, antioxidants, colorants, pigments non-radioopaque fillers, and compatible combinations of two or more of the foregoing.

28. The method of claim 19, wherein the cross-linker component comprises one or more of compounds containing functional groups selected from the group consisting of acryl, (meth) acryl, vinyl, propenyl, butenyl, pentenyl, hexenyl, octenyl, allyl, alkenyloxy, alkenylamino, allyloxy, allylamino, furanyl, phenyl and benzyl.

29. The method of claim 19, wherein wherein the cross-linker component is selected from the group consisting of triallyl cyanurate, trimethylolpropane triacrylate, melamine cross-linkers, tolylene 2,4-diisocyanate, organohydrogenpolysiloxane cross-linkers, and epoxy cross-linkers.

30. The method of claim 19, wherein the free radical source material comprises one or more of benzoin, substituted benzoins, benzopheone, benzopheone derivatives, Michler's ketone, alphahydroxyketone, benzildimethylketal, isopropylthioxanthane, dialkoxyacetophenones, acetophenone, benzil, and other derivatives (substituted forms) and mixtures thereof.

31. The method of claim 19, wherein the article comprises a tubular article whose outer tubular surface is surfacially cross-linked.

32. The method of claim 19, wherein the article comprises a generally J-shaped tubular article.

33. The method of claim 19, wherein the article is of tubular form.

34. The method of claim 19, wherein the article comprises a main linear portion and a distal curvate portion, wherein the distal curvate portion is surfacially cross-linked to a different extent than the main linear portion.

35. The method of claim 19, wherein said precursor structure been constrained in a curved conformation as said initial shape, and exposed in the constrained curved conformation to said ultraviolet radiation.

36. The method of claim 19, wherein the elastoplastic material comprises polyester, polyamide, polyurethane or a polyether/polyamide block copolymer, the cross-linker component comprises trimethylolpropane triacrylate or triallylcyanurate, and the free-radical source material comprises benzildimethylketal or benzophenone.

\* \* \* \* \*

UNITED STATES PATENT AND TRADEMARK OFFICE
CERTIFICATE OF CORRECTION

PATENT NO. : 6,291,543 B1  Page 1 of 1
DATED : September 18, 2001
INVENTOR(S) : Tilak M. Shah It is certified that error appears in the above-identified patent and that said Letters Patent is hereby corrected as shown below:

Column 1,
Line 37, "artery). Catheters" should be -- artery). ¶ Catheters --

Column 2,
Line 19, "Surfacial" should be -- surfacial --
Line 36, "confirmations" should be -- conformations --
Line 49, "being, UV" should be -- being UV --

Column 4,
Line 2, "alplhahydroxyketone" should be -- alphahydroxyketone --
Line 3, "dialkoxyacetophelnones" should be -- dialkoxyacetophenones --

Column 6,
Line 12, ""J", shape" should be -- "J" shape --
Line 40, "FIG. 1 as" should be -- FIG. 1. As --
Line 53, "another-," should be -- another, --
Line 65, "manners" should be -- manner, --

Signed and Sealed this

Nineteenth Day of August, 2003

JAMES E. ROGAN
*Director of the United States Patent and Trademark Office*